United States Patent [19]

Benecke et al.

[11] Patent Number: 5,332,839

[45] Date of Patent: * Jul. 26, 1994

[54] CATALYTIC PRODUCTION OF LACTIDE DIRECTLY FROM LACTIC ACID

[75] Inventors: Herman P. Benecke; Richard A. Markle; Richard G. Sinclair, all of Columbus, Ohio

[73] Assignee: BioPak Technology, Ltd., Golden, Colo.

[ * ] Notice: The portion of the term of this patent subsequent to Oct. 26, 2009 has been disclaimed.

[21] Appl. No.: 584,466

[22] Filed: Sep. 18, 1990

[51] Int. Cl.$^5$ .............................................. C07D 319/12
[52] U.S. Cl. .................................... 549/274; 203/14
[58] Field of Search ........................... 549/274; 203/14

[56] References Cited

U.S. PATENT DOCUMENTS

| | | | |
|---|---|---|---|
| 1,095,205 | 5/1914 | Gruter et al. | 549/274 |
| 1,594,843 | 8/1926 | Lawrie | 203/89 |
| 1,995,970 | 3/1935 | Dorough | 260/2 |
| 2,163,268 | 6/1939 | Carothers et al. | 260/338 |
| 2,174,491 | 9/1939 | Watson | 260/67 |
| 2,189,572 | 2/1940 | Watson | 260/78 |
| 2,668,162 | 2/1954 | Lowe | 260/78.3 |
| 2,703,316 | 3/1955 | Schneider | 260/78.3 |
| 2,758,987 | 8/1956 | Salzberg | 260/78.3 |
| 2,768,973 | 10/1956 | Castle et al. | 260/602 |
| 3,322,719 | 6/1967 | Peilstöcker | 260/45.8 |
| 3,435,008 | 3/1969 | Schmitt et al. | 260/78.3 |
| 3,457,280 | 7/1969 | Schmitt et al. | 260/340.2 |
| 3,597,450 | 8/1971 | Schmitt et al. | 260/340.2 |
| 3,736,646 | 6/1973 | Schmitt et al. | 29/458 |
| 3,867,190 | 2/1975 | Schmitt et al. | 117/138.8 |
| 3,960,152 | 6/1976 | Augurt et al. | 128/335.5 |
| 4,033,938 | 7/1977 | Augurt et al. | 260/78.3 |
| 4,070,375 | 1/1978 | Suzuki | 549/274 |
| 4,727,163 | 2/1988 | Bellis | 549/274 |
| 4,797,468 | 1/1989 | DeVries | 549/274 |
| 4,835,293 | 5/1989 | Bhatia | 549/274 |
| 4,966,982 | 10/1990 | Ono et al. | 549/274 |
| 4,990,222 | 2/1991 | Aigner et al. | 203/91 |
| 5,023,349 | 6/1991 | Bhatia | 549/274 |
| 5,023,350 | 6/1991 | Bhatia | 549/274 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,068,418 | 11/1991 | Kulprathipanja et al. | 562/580 |
| 5,075,115 | 12/1991 | Brine | 424/486 |
| 5,089,632 | 2/1992 | Paul | 549/274 |
| 5,091,544 | 2/1992 | Bhatia | 549/274 |

FOREIGN PATENT DOCUMENTS 863673 2/1971 Canada .

(List continued on next page.)

OTHER PUBLICATIONS

Bezzi et al., "Dehydration Products of Lactic Acid Typifying the Transformation of Cyclic Esters into Linear Polyesters", Meeting of the Italian Academy of Science, Nov., 1936.

(List continued on next page.)

Primary Examiner—C. Warren Ivy
Assistant Examiner—A. A. Owens
Attorney, Agent, or Firm—Sheridan Ross & McIntosh

[57] ABSTRACT

The present invention is directed to a method for making lactide from aqueous lactic acid. The invention method comprises converting feed aqueous lactic acid to its vapor phase. The feed vapors then are passed through a reactor maintained at elevated temperature and in which optionally is disposed an alumina catalyst. Withdrawn from the reactor is product lactide, water, and unreacted lactic acid which are subjected to separation for recovery of the lactide product. The separated unreacted lactic acid is eligible for readmission to the process for making additional lactide. This cyclic process embodiment of the present invention comprises the steps of passing make-up aqueous lactic acid feed into a vaporization zone along with unreacted aqueous lactic acid filtrate from another step of the process and therein forming aqueous lactic acid feed vapors. The thus-generated vapors that are passed through a vapor phase reaction zone held at elevated temperature for forming lactide therein. Lactide as a solid is separated from unreacted aqueous lactic acid filtrate; and the filtrate is passed into the vaporization zone in the initial step of the process.

18 Claims, 1 Drawing Sheet

FOREIGN PATENT DOCUMENTS

| | | |
|---|---|---|
| 871135299 | 9/1987 | European Pat. Off. . |
| 871153847 | 10/1987 | European Pat. Off. . |
| 0275581 | 7/1988 | European Pat. Off. . |
| 221786 | 5/1910 | Fed. Rep. of Germany . |
| 267826 | 12/1913 | Fed. Rep. of Germany . |
| 53074 | 5/1967 | Fed. Rep. of Germany . |
| 36321036 | 9/1986 | Fed. Rep. of Germany . |
| WO91/17155 | 11/1991 | PCT Int'l Appl. . |
| WO92/00292 | 1/1992 | PCT Int'l Appl. . |
| 1007347 | 9/1964 | United Kingdom . |
| 1122229 | 7/1968 | United Kingdom . |

OTHER PUBLICATIONS

Bischoff et al., "Ueber Das Glycolid und Seine Homologen", pp. 262–265, 1893, Chem. Ber., vol. 26.

Carothers et al., "Studies of Polymerization and Ring Formation. X. The Reversible Polymerization of Six-Membered Cyclic Esters", pp. 761–771, 1932, J. Am. Chem. Soc., vol. 54.

Carothers, "Polymers and Polyfunctionality", pp. 39–53, 1936, Transactions of the Faraday Society, vol. 32.

Deibig et al., "I. Synthesis and Properties of Polytetramethyl Glycolide", pp. 123–131, 1971, Die Makromolekulare Chemie, vol. 145.

Deibig et al., "III. Thermal Behavior of Polytetramethyl Glycolide", pp. 133–139, 1971, Die Makromolekulare Chemie, vol. 145.

Dietzel et al., "Über Das Chemische Gleichgewicht Zwischen der Milchsäure und Ihren Anhydriden in Wäbriger Lösung", pp. 1307–1314, 1925, Chem. Ber., vol. 58B.

Filachione et al., "Lactic Acid Condensation Polymers: Preparation by Batch and Continuous Methods", pp. 223–228, 1944, Industrial and Engineering Chemistry, Mar., vol. 36, No. 3.

Hill et al., "Cyclic and Polymeric Formals", pp. 925–928, 1935, J. Am. Chem. Soc., vol. 57.

Holten, "Lactic Acid. Properties and Chemistry of Lactic Acid and Derivatives", pp. 221–231, 1971, Verlag Chemie.

Imasaka et al., "Synthesis of Degradable Terpolymers Responding to External Stimuli Such as pH, Ionic Strength, and Temperature", pp. 715–722, 1991, Makromol. Chem. vol. 192.

Ikada et al., "Stereocomplex Formation Between Enantiomeric Poly(Lactides)", pp. 904–906, 1987, American Chemical Society, Macromolecules, 20.

Jackanicz et al., "Polylactic Acid as a Biodegradable Carrier for Contraceptive Steroids", pp. 227–234, 1973, The Population Counsel, Sep., vol. 8, No. 3.

Jungfleisch et al., "Oragnic Chemistry—On the Dilactide of Left Lactic Acid", pp. 637–639, 1906, Academie Des Sciences, Meeting of Mar. 12.

Kleine et al., "High Molecular Weight, Especially Optically Active Polyesters of Lactic Acid: An Investigation of the Stereochemistry of Macromolecular Compounds", pp. 1–21, 1958, Report from the Research Laboratory for Macromolecular Chemistry, Dec.

Kulkarni et al., "Polylactic Acid for Surgical Implants", pp. 839–843, 1966, Arch. Surg., vol. 93, Nov.

Light, "Lactic Acid Resins", pp .135–136, 1940, Paint Manufacture, Jun.

Watson, "Composition of Lactic Acid. Production of a Highly Concentrated Acid", pp. 399–401, 1940, Industrial and Engineering Chemistry, vol. 32, No. 3.

Wise, "Biopolymeric Controlled Release Systems", pp. 3–28, 1984, CRC Press, vol. 1.

Wise, "Biopolymeric Controlled Release Systems", pp. 187–199, 1984, CRC Press, vol. 2.

Wise, et al., "Lactic/Glycolic Acid Polymers", pp. 237–270, Dynatech R/D Company, Cambridge, Mass., U.S.A. (no date available).

CATALYTIC PRODUCTION OF LACTIDE DIRECTLY FROM LACTIC ACID

BACKGROUND OF THE INVENTION

The present invention relates to the catalytic production of lactide and more particularly to its production directly from lactic acid.

For purposes of this application, the following definitions apply:

$L_1A$: lactic acid or 2-hydroxypropionic acid
LD: lactide or 3,6-dimethyl-1,4-dioxane-2,5-dione
$L_2A$: lactoyllactic acid or lactic acid dimer
$L_3A$: lactoyllactoyllactic acid or lactic acid trimer
$L_nA$: n-oligomer of lactic acid.

The DP or degree of polymerization of lactic acid is "n".

Lactic acid has one asymmetric carbon atom and, thus, can be found in two enantiomeric forms. Lactide, on the other hand, has two asymmetric carbon atoms so that it can be found in three steroisomeric forms: L-lactide in which both asymmetric carbon atoms possess the L (or S) configuration; D-lactide in which both asymmetric carbon atoms possess the D (or R) configuration; and meso-lactide in which one asymmetric atom has the L configuration and the other has the D configuration. L-lactide and D-lactide are enantiomers while D,L-lactide is the meso species. In the production of lactide from lactic acid, it would be advantageous if the absolute configuration of the lactic acid feed was maintained in its conversion to lactide. Enantiomeric lactide, especially L-lactide, has utility in the production of polymers, especially in the production of environmentally degradable polymers such as proposed in commonly-assigned U.S. applications Ser. Nos. 387,670; 387,676; 387,678; and 386,844.

Heretofore, production of lactide from lactic acid has proceeded by the initial formation of oligomeric lactic acid, $L_nA$, such as by dehydration of aqueous lactic acid, followed by a catalytic transesterification reaction known as "back-biting" as illustrated below:

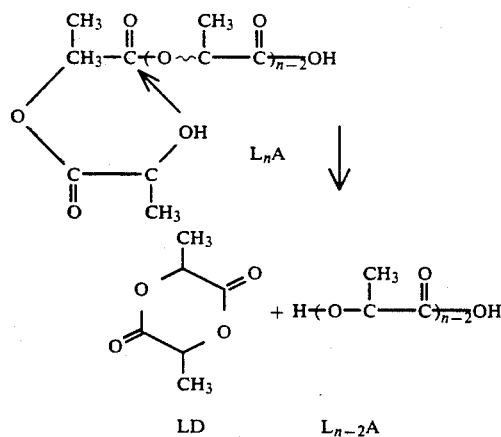

As illustrated above, back-biting depolymerization of $L_nA$ results in the production of lactide. Catalysts proposed for such a reaction include tin powder, tin halides, or tin carboxylates (EP Publication 261,572); tin alkoxides (U.K. Pat. No. 1,007,347); and zinc or tin (EP Publication 264,926).

Direct conversion of lactic acid into lactide with or without preservation of absolute configuration of asymmetric atoms is not shown in the art.

BROAD STATEMENT OF THE INVENTION

Aqueous lactic acid for present purposes comprehends an aqueous mixture of one or more of $L_1A$, $L_2A$, and $L_3A$, optionally with LD being present. The present invention is directed to a flow process for making L-lactide from aqueous L-lactic acidified. The inventive method comprises converting feed aqueous lactic acid to its vapor phase. L-lactic acid is the preferred feed configuration for making L-lactide, and is to be understood even though the configuration symbol is not used throughout this application. The feed vapors then are passed through a reactor maintained at elevated temperature and in which optionally is disposed an alumina catalyst. Withdrawn from the reactor is product lactide, water, and unreacted aqueous lactic acid feed which are subjected to separation for recovery of the lactide product.

The separated unreacted lactic acid feed is eligible for readmission to the process for making additional lactide. This cyclic process embodiment of the present invention comprises the steps of passing make-up aqueous lactic acid feed into a vaporization zone along with unreacted aqueous lactic acid filtrate from another step of the process and therein forming aqueous lactic acid feed vapors. The thus-generated vapors then are passed through a vapor phase reaction zone held at elevated temperature for forming lactide therein. Lactide as a solid is separated from unreacted aqueous lactic acid filtrate; and the filtrate is recycled into the vaporization zone in the initial step of the process.

Advantages of the present invention include the ability to convert aqueous lactic acid directly into lactide of high purity. Another advantage is that the asymmetric carbon atoms in product lactide predominate in the same absolute configuration as the feed aqueous lactic acid from which it is made. Another advantage is a process which is amenable to recycling unreacted aqueous lactic acid. Yet a further advantage is a process in which little unwanted by-product formation results. These and other advantages will be readily apparent to those skilled in the art, based upon the disclosure contained herein.

Figure 1:
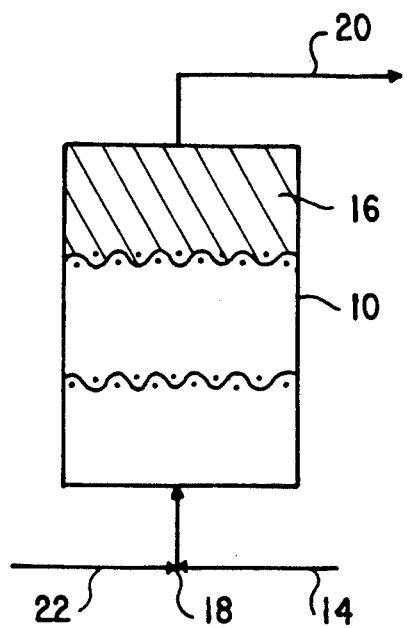
FIG. 1 is a schematic representation of the laboratory reactor used in the examples.

The drawings will be described in detail below.

DETAILED DESCRIPTION OF THE INVENTION

The lactic acid feed is in aqueous form for conversion to its vapor phase as an initial step of the process of the present invention. The role played by water in the process can be appreciated by reference to the following equilibrium reactions:

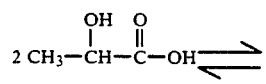

-continued

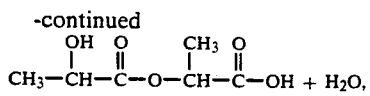

or written another way:

etc.

Thus, it will be observed that $L_1A$ is in equilibrium with higher oligomers of lactic acid and water. By removing water, these reactions shift to the right. In fact, $L_2A$ and higher lactic acid oligomers ($L_nA$) are made by dehydrating aqueous lactic acid. Sufficient water, then, should be present so that the equilibrium detailed above favors the presence of $L_1A$, $L_2A$, and $L_3A$ as the feedstock. Extra quantities of water in the feedstock are permissible at the expense of the handling and energy costs associated therewith.

The aqueous lactic acid feedstock is converted to its vapor phase for passing into a vapor phase reaction zone. Liquid phase aqueous lactic acid in the reaction zone containing catalyst results in much lower lactide yields and a lower purity lactide product, compared to use of vapor phase lactic acid feed. Thus, it is desirable that the feed aqueous lactic acid be converted to its vapor phase prior to its entrance into the reaction zone. It should be recognized, however, that some liquid phase lactic acid is tolerable in the feed at the expense of lactide product.

Since conversion of lactic acid (or more properly oligomers thereof) into lactide has been a catalytic process in the art, initial research endeavors for directly converting $L_1A$ into LD focused on selection of a catalyst(s) that would be effective for the direct conversion of $L_1A$ into LD. While such research endeavors proved fruitful, unwanted degradation by-products, chiefly carbon monoxide (CO) and acetaldehyde, always were present, thus lowering the effective yields of $L_1A$ into LD even when recycle techniques were employed. While glass beads alone permitted direct conversion of $L_1A$ into LD, it appeared that the catalyst was not essential to the process. This led to the fundamental discovery that when $L_1A$ (or its dimer, $L_2A$ or trimer, $L_3A$) is converted to its corresponding vapor and passed through a reaction zone held at elevated temperature, LD was formed (albeit at reduced levels compared to the use of a catalyst) and CO was at or below the detection limits of the instruments being used. Thus, the invention broadly comprehends the direct conversion of $L_1A$, $L_2A$ or $L_3A$ into LD in a vapor phase reaction which preferably is conducted as a flow process utilizing the assistance of a carrier gas for passing reactants into and through the reaction zone and for withdrawing a product stream therefrom. Since the crude LD product stream contains virtually only $L_1A$ (i.e. virtually no $L_nA$ oligomers), the process is especially amenable to being cyclic for substantially increasing the overall yield of LD from feed lactic acid. A fundamental recognition of the present invention is that LD is sufficiently stable in the presence of hot $L_nA$ and water that it can be isolated.

Since water is in the feed and water of reaction is present in the reactor, the process is conducted under hydrous conditions. Likely, this means that $L_3A$ vapors may be converted to $L_2A$ plus $L_1A$. Since $L_2A$ is believed to be the species that cyclizes to form LD, $L_2A$ formation from $L_1A$ and $L_3A$ benefits the yield of LD.

At this juncture, it is worth restating the equilibrium equations discussed initially. "Lactic acid" as a stock chemical item is not pure $L_1A$ in water, but rather is an equilibrium mixture of $L_1A$ with higher oligomeric species depending upon concentration of $L_1A$ and water, temperature, and other factors. The art has always dealt with $L_5A$ and higher oligomeric species for conducting a back-biting reaction for LD production. The present invention is unique in that the lactic acid feed, regardless of initial composition, is processed or equilibrated to be enriched primarily in $L_1A$ and $L_2A$, and some $L_3A$, and depleted in higher $L_nA$ oligomers. Thus, feed lactic acid for present purposes comprehends $L_1A$, $L_2A$, $L_3A$, and mixtures thereof, optionally with LD being present. Since an equilibrium reaction involving water always occurs, minor amounts of higher oligomeric species may be present in the feed lactic acid and, though not desired, can be tolerated in minor amounts.

When the unreacted aqueous lactic acid from the product stream is separated from lactide after water washing, it too can be processed, for example by distillation, for re-establishing a desired feed and for blending with additional make-up feed lactic acid which similarly may be treated. Since two product streams are being combined into a composite product stream for recycle to the vapor phase reaction zone, each is treated and/or adjusted in $L_1A$, $L_2A$, and $L_3A$ content for producing a desired recycle feed stream for admission into the vapor phase reaction zone for production of LD.

As noted above, lactide yields can be significantly increased (e.g. up two-fold or more) by contacting the lactic acid feed vapors with a catalyst disposed within the vapor phase reaction zone. Since the catalyst also increases the degradation by-product formation, primarily CO and acetaldehyde, the operator has the opportunity to control yields, selectivity, and economics of the process by judicious selection of the inclusion of and types of catalyst used in the process.

With respect to catalysts which optionally may be housed within the vapor phase reaction zone, alumina catalyst appears to be preferred in improving LD yields while minimizing CO by-product formation. Other catalysts which display some activity include alumina-silica combinations and zeolites. Acidic catalysts including silica gel, phosphoric acid/Kieselguhr, and Amberlyst acid ion exchange resins, tend to favor CO production almost to the point of excluding LD production. Catalyst particle sizes ranging from about 2 to 6 mm have been tested and found functional, though yields do vary with catalyst particle size.

The process preferably is conducted by passing lactic acid feed vapors with aid of a hot carrier gas through the vapor phase reaction zone which optionally, contains a bed of alumina catalyst. The carrier gas can be an inert gas, such as nitrogen, or can be a condensable gas such as an organic material. The carrier gas aids in carrying the lactic acid vapors into the reactor and sweeping lactide and water products therefrom. Vapor pressure considerations indicate that $L_1A$ and water will predominately vaporize in the hot carrier gas, whereas higher molecular weight lactic acid oligomeric species have decreasing vaporization tendencies with increasing molecular weights. In a properly designed reaction apparatus, the combined hot carrier gas and aqueous lactic acid feed could be continuously passed through feed material which is depleted in $L_1A$ by virtue of its preferential vaporization into the vapor phase reaction zone. The feed also will be depleted in $L_2A$ by cyclization to LD, vaporization, or both. Presently, the fate of $L_2A$ during the vaporization step is unconfirmed vis a vis whether $L_2A$ cyclizes, and LD vaporizes and then cyclizes, or a combination. This type of arrangement would permit the hot water liquid and vapor from the fresh feed to hydrolyze non-vaporized oligomeric lactic acid species towards $L_1A$ and $L_2A$ which will readily be vaporized in the hot carrier gas. This technique is referred to as in situ hydrolysis/vaporization. This technique also permits improved LD yields by converting lactic acid oligomeric species into $L_1A$ and $L_2A$ which can be directly converted into LD in accordance with the precepts of the present with the precepts of the present invention. The presence of water in the reactor assists in suppressing the formation of higher $L_nA$ oligomers.

Exhaustive testing of the present invention has revealed that the stereospecificity of the reaction is about 90% to 99% in product L-lactide with the balance typically being meso-lactide. Little L-lactic acid decomposition occurs as evidenced by the low carbon monoxide and very low acrylic acid contents of the products exiting the reactor.

Figure 2:
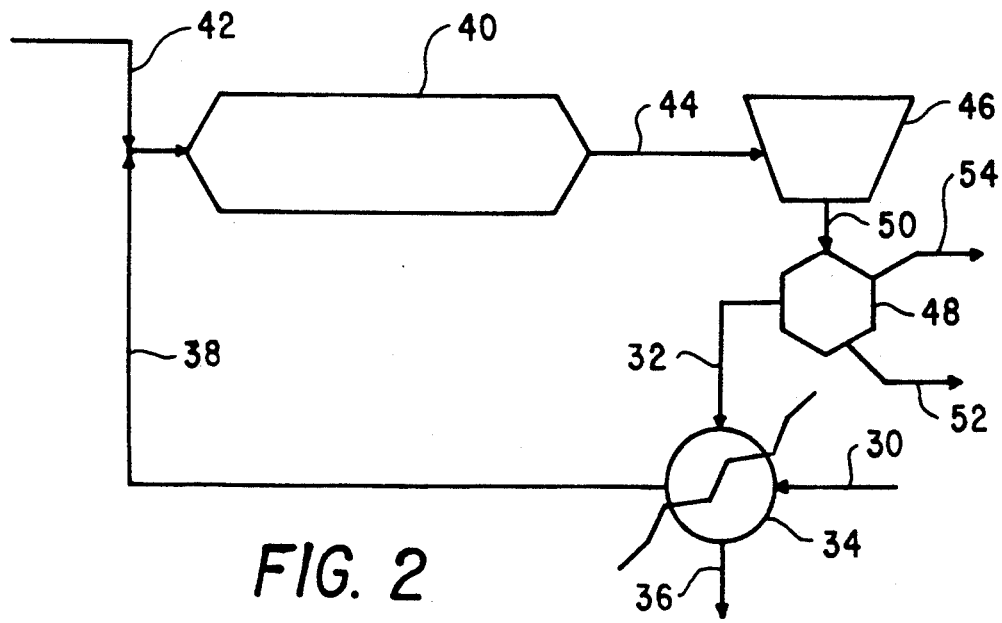
FIG. 2 is a flow diagram representing a cyclic process for making lactide from aqueous lactic acid feed in accordance with the present invention.

The cyclic process for making LD from aqueous lactic acid can be envisioned in a variety of configurations. One such configuration is set forth at FIG. 2. With respect to FIG. 2, make-up aqueous lactic acid feed 30 and unreacted lactic acid filtrate 32 from another step of the process are passed into heating zone 34 which can be a pot or distillation scheme configured appropriately. Water is distilled from the contents in heating zone 34 and withdrawn via line 36. Lactide may also be present in stream 36 and can be filtered therefrom by appropriate cooling of the steam vapors withdrawn in line 36. Sufficient water removal is accomplished in zone 34 to provide one or more of $L_1A$, $L_2A$, $L_3A$. In this regard, reference is made to commonly-assigned application Ser. No. 584,126, filed on even date herewith, of Sinclair, et al. The Sinclair, et al. process makes LD from liquid aqueous lactic feed by subjecting the feed to heating to distill water therefrom until the heated feed has a DP not substantially above about 2, and then ceasing heating to provide a crude LD product. Such process may be quite advantageous to employ for treating the recycle stream in zone 34 for admission to reactor 40.

Once the desired lactic acid feedstock composition has been achieved, such feedstock is withdrawn via line 38 and passed into reactor 40 along with hot carrier gas flow 42. Carrier gas 42, preferably nitrogen, has been heated to an appropriate reaction temperature for combining with aqueous lactic acid feedstock 38 and assists in the vaporization of $L_1A$ and water (and cyclization/vaporization or vice versa of $L_2A$) for passing through the vapor phase reaction zone housed within reactor 40. As discussed above, a variety of configurations for forming aqueous lactic acid vapors can be envisioned. Reactor 40 optionally may contain a bed of catalyst also.

Lactide product is withdrawn from reactor 40 and passed via heated line 44 into collection zone 46 which suitably can be a cyclone or similar apparatus with tangential flow. At laboratory scale operation, cyclone 46 was maintained cold (about 10° C. to −78° C.). At 10° C., the LD preferentially collected as a crystalline layer below the inlet tube and the $L_1A$ collected as a liquid in the bottom of cyclone 46. At −78° C., the LD collected as a crystalline mass directly below the inlet tube and the LA solid collected elsewhere along the walls thereof. The interior surface of vessel 46 then was scraped and washed with cold water and the contents passed into separation zone 48 via line 50. In separation zone 48, the cooled material was stirred and subjected to filtration for removal of product lactide via line 52. LD typically was dried under vacuum in the presence of phosphorous pentoxide to remove tightly bound water. Gases withdrawn via line 44 from reactor 40 are collected via line 54 and passed through various traps in order to condense condensable material contained therein. The filtrate from separation zone 48 is then passed via line 32 back into heating zone 34 to complete the cyclic process.

It will be appreciated that a variety of collection/separation schemes can be envisioned with respect to separation of product lactide from unreacted aqueous lactic acid. So long as product lactide is separated from unreacted lactic acid for recycle, an efficacious cyclic process for making lactide directly from $L_1A$ ensues.

The following examples show how the present invention has been practiced, but should not be construed as limiting. In this application, all percentages and proportions are by weight and all units are in the metric system, unless otherwise expressly indicated. Also, all citations referred to herein are incorporated expressly herein by reference.

IN THE EXAMPLES

The laboratory scale reactor used in the Examples is set forth schematically at FIG. 1. Reactor 10 is a stainless steel reactor having a width of about 5 cm and a height of about 31 cm. Reactor 10 was fitted with lower screen 12 (which may be a series of screens) and upper screen 14 (which also may be more than one screen). Catalyst bed 16 was disposed atop screen 14. The lower empty chambers provided additional time to ensure that the lactic acid feed was converted to its vapor phase via in situ hydrolysis/volatilization prior to its contact with the catalyst bed. Reactor 10 was fitted with lower Tee 18 and upper heated product line 20 for withdrawal of the lactide product. L-lactic acid was fed into Tee 18 via line 22. Nitrogen carrier gas was passed into admixture with lactic acid feed by line 24 which connected to Tee 18. This entire assembly was placed in a sand bath which was heated to maintain the desired reactor temperature. Broadly, the reaction temperature should be greater than about 150° and can range on up to as high as about 225° C. Nominal reaction temperatures around 205° C. were found acceptable using reactor 10. Space times of about 0.8 to 3 seconds also were found acceptable.

EXAMPLE 1

The experimental reactor depicted in FIG. 1 was modified so that screen 12 was a 100 mesh screen laid adjacent a 16 mesh screen and screen 14 was actually a 45 mesh screen overlaying a 16 mesh screen. Catalyst 16 comprised 10-20 mesh silica gel/alumina catalyst (Akzo-$L_1A$-30-5P catalyst, 87% silica/13% alumina, Akzo Chemicals B.V.). The nitrogen flow rate was adjusted to 1600 ml/min. and it plus the lactic acid feed were passed through reactor 10 at a superficial vapor velocity of 0.12 ft/sec. The space time of the contents was 2.8 seconds. Lactic acid feed comprised commercial "85% lactic acid" (61% L-lactic acid, 20% L-L,lactoylactic acid, 4% L,L,L-lactollactoyllactic acid, and 15% water) which had been diluted with an additional 11% by weight of water just prior to the run. This feedstock was passed into Tee 18 for admixture with nitrogen at a flow rate of 36.6 ml/hr. The results recorded are set forth below:

TABLE 1

| Stage (44701-90) | Cumulative Time (hr) | Bed Temp. (°C.) | $L_1A$ Feed (g) | All* Products (g) | LD Product (g) | LD Yield (mole-%) |
|---|---|---|---|---|---|---|
| Equilibration | 1.8 | 206 | 75.5 | 53.2 | 8.46 | — |
| 1 | 4.8 | 205 | 128.6 | 115.8 | 22.73 | 25.7 |
| 2 | 8.1 | 204 | 141.1 | 130.6 | 28.31 | 30.1 |

*Catalyst weight gain: 21.8 g
Trap contents: 3.8 g
Reactor residue: 1.3 g
Total Material Recovery: 94.6 wt-%

The above-tabulated data demonstrates that in situ hydrolysis/volatilization is feasible since the reactor lower chambers were found to be empty and the removed ground catalyst was bone dry. The lactic acid feedstock containing an extra 11% water in addition to the 15% water already in the commercial lactic acid facilitated in situ hydrolysis/volatilization. It is believed that this extra water serves a beneficial effect since screen clogging of the lower set of screens did not occur as it did by reference to Example 2 using undiluted 85% lactic acid. The product lactide was found to have a purity of 89% at Stage 1 and 92% at Stage 2 and was a white powder. Carbon monoxide production was 2750 ppm after 2.5 hours. This corresponds to 3.3% lactic acid decomposition. The ratio of the lactide yield obtained at Stage 2 to the mole percent lactic acid decomposed is 9.1:1. The LD purity for Stage 1 was 89 wt-% and for Stage 2 it was 92 wt-%. The L-LD:meso-LD weight ratio was 51.8:1 for Stage 1 and 34.1:1 for Stage 2.

The catalyst weight gain of 21.8 g was obtained upon stopping the lactic acid feedstock and nitrogen flows immediately after completion of the run. The catalyst bed was not stripped with continuing hot nitrogen flow. This catalyst weight gain is believed indicative that significant material loading occurred to a presumed steady state during the run. Due to the construction of the reactor, the catalyst bed undergoes a slow cool-down in the sand bed so the composition of the adsorbed species would be expected to change significantly before the bed can be removed and examined. All precedents indicate that $L_nA$ species will undergo significant oligomerization during this cool-down period.

EXAMPLE 2

This run was conducted in order to evaluate the in situ hydrolysis/vaporization approach by using undiluted lactic acid feedstock. The amount of water present in 85% lactic acid is approximately five-fold greater than that required to hydrolyze all ester functionality in $L_2A$ and $L_3A$ to LA. The question is whether the ratio of the hydrolysis rate in the liquid state to the water vaporization rate is sufficient to allow complete hydrolysis of oligomeric lactic acid.

The procedure described in connection with Example 1 was repeated using 85% lactic acid feedstock at 32.9 ml/hr and the same nitrogen flow rate to yield a space time of 3.0 seconds and a superficial velocity of 0.11 ft/sec. The results recorded are set forth below.

TABLE 2

| Stage (44853-9) | Cumulative Time (hr) | Bed Temp. (°C.) | $L_1A$ Feed (g) | All* Products (g) | LD Product (g) | LD Yield (mole-%) |
|---|---|---|---|---|---|---|
| Equilibration | 1.9 | 205 | 74.4 | 48.9 | 11.91 | — |
| 1 | 5.1 | 204 | 123.6 | 106.1 | 29.73 | 31.6 |
| 2 | 8.4 | 204 | 132.0 | 119.0 | 32.53 | 34.0 |
| Post-Run | 9.6 | 202 | — | 8.2 | — | — |

*Catalyst weight gain: 10.66 g
Trap Contents: 1.32 g
Reactor residue: 0.81 g
Total Material Recovered: 89.4 wt-%

As the above tabulated data reveals, the lactide yield (34%) obtained in Stage 2 is higher than that obtained in Example 1. The higher lactide yield compared to Example 1 could have resulted from the decreased percent water in the lactic acid feed. Recovered percentages of lactide were found to steadily increase during each stage. The overall recovery of 89.4% of the material fed is lower than the recovery in Example 1. An error in determining the tare or final collector weight could have contributed to this low number. In a duplicate run, the overall recovery of material fed was 94.1%, but lower LD/CO ratios were seen.

The carbon monoxide concentrations were 3200 ppm after 3.2 hours, 2,750 ppm after 5.1 hours, and 2800 ppm after 8.0 hours. The average CO concentration between 3.2 and 8 hours of operation corresponds to 3.2 wt-% lactic acid decomposition. The ratio of the lactide yield obtained during Stage 2 to the mole percent lactic acid decomposed is 10.7:1, which is higher than the value computed in Example 1.

The product lactide obtained from Stages 1 and 2 was a white powder. The L-LD:meso-LD weight ratio was 44.0 for Stage 1 and 38.6 for Stage 2. The lower 100 mesh screen was partially clogged after the run was completed, indicating that in situ hydrolysis/vaporization was not as effective as in example 1 which employed a higher water content in the $L_1A$ feed. However, the removed catalyst bed was found to be bone dry.

The filtrate from Stage 1 was extracted with methylene chloride to recover any solubilized lactide which had not yet hydrolyzed. A yellow liquid was obtained from the rotary evaporator (5.4 g) which did not solidify at 52° C. after the methylene chloride was removed. Upon cooling to room temperature, however, this material solidified to a white crystalline mass which contained a minor amount of yellow liquid. This mixture was washed with cold water to obtain 1.9 g of a white solid which was analyzed to contain 87.4% L-lactide and 12.6% meso-lactide.

EXAMPLE 3

This run was conducted in order to determine the efficacy of 5 mm catalyst pellets rather than the 10/20 mesh catalyst used in Example 2. The same conditions as obtained in Example 2 were maintained here, except that the 85% lactic acid flow rate was 34.6 ml/hr and the lower 100 mesh screen had been removed. The following results were recorded.

TABLE 3

| Stage (44853-21) | Cumulative Time (hr) | Bed Temp. (°C.) | $L_1A$ Feed (g) | All* Products (g) | LD Product (g) | LD Yield (mole-%) |
|---|---|---|---|---|---|---|
| Equilibration | 2.0 | 205 | 84.0 | 58.5 | 15.34 | — |
| 1 | 5.2 | 206 | 127.2 | 111.1 | 25.91 | 28.8 |
| 2 | 7.7 | 204 | 108.6 | 87.7 | 20.65 | 26.4 |
| 3 | 11.0 | 220 | 136.8 | 142.6 | 43.49 | 44.6 |
| Post-Run | 11.8 | 217 | — | — | — | — |

*Catalyst weight gain: 18.35 g
Trap Contents: 1.99 g
Reactor residue: 0.07 g
Total Material Recovered: 92.0%

The lactide yields obtained at approximately 205° C. appear to be slightly decreasing with time after the equilibration stage was completed. Note that the percent recovery obtained during Stage 2 (80.8%) also decreased compared to Stage 1 (87.3%). This behavior is opposite to that observed with the smaller particle size catalyst in Examples 1 and 2.

Carbon monoxide production was recorded at 6,000 ppm after 1.5 hours, 3,650 ppm after 4.8 hours, 3,550 ppm after 6.3 hours, and 9,000 ppm after 10.8 hours. The carbon monoxide concentration, then, appeared to decrease after the equilibration stage to a fairly constant value at the nominal 205° C. bed temperature. The calculated mole percent lactic acid decomposed was 3.9% during Stages 1 and 2. The ratio of the lactide yield obtained during Stage 2 to the mole percent lactic acid decomposed was 6.7:1. This ratio is 37% lower than the ratio obtained with the smaller sized catalyst in Example 2. Thus, the total yield expected under recycle conditions should be significantly higher with the smaller size catalyst compared to the use of larger size catalyst for the same reactor conditions.

After 7.7 hours of operation at approximately 205° C., the temperature of the catalyst bed was raised to approximately 220° C. and maintained at this temperature for 3.3 hours. The total weight of material collected over this time was 104% of the material fed during this same time period. Similarly, the lactide yield of 44.6% observed for this time period is inflated by the fact that part of the lactide collected probably originated from the earlier part of the run conducted at 205° C., i.e., lactide produced from residual $L_nA$ deposited on the catalyst bed earlier. However, the apparent increased lactide yield obtained at this temperature is more than compensated by the increased carbon monoxide production, viz. lactic acid decomposition. The ratio of the lactide yield to the mole percent lactic acid decomposed can be estimated to be no higher than about 4.5:1. The L-LD:meso-LD weight ratio was approximately 42 for Stages 1 and 2, but only 25.3 for Stage 3. Thus, operating at higher bed temperatures with this larger sized particle catalyst and reactor design would be expected to lead to reduced L-LD:meso-LD selectivities and reduced lactide yields, when recycle of unreacted $L_1A$ is considered.

After the run was completed, partial clogging of the lower 16 mesh screen was noted. As also indicated in Example 2, complete in situ hydrolysis/vaporization apparently was achieved because the removed catalyst bed was found to be bone dry. This clogging probably occurred during cool-down since the gaseous back-pressure did not increase during the entire run.

EXAMPLE 4

The reactor was filled with alternating layers of 3 mm glass beads and the silica alumina catalyst described in Example 1 as follows: glass 125 ml; catalyst 23 ml; glass 160 ml; catalyst 22 ml; glass 70 ml; catalyst 22 ml; and glass 70 ml, from top to bottom. The 85% lactic acid feed was passed into the reactor at a rate of 16.5 ml/hr with a nitrogen sweep at 800 ml/min. which establishes a space time of about 2.7 sec (catalyst only) and superficial velocity of 0.04 ft/sec. The reactor temperature was maintained at about 203°=3° C. The product was washed with cold water and the lactide filtered therefrom. The lactide then was dried by slight heating under vacuum in the presence of $P_2O_5$. The filtrate was collected and subjected to distillation to remove sufficient water to re-establish a lactic acid concentration similar to the original 85% feed lactic acid. This distilled filtrate was then combined with make-up 85% lactic acid and recycled to the reactor. This sequence was repeated for 3 reaction stages; however the start-up stage suffered from equipment leaks so that it was excluded from calculations.

In total, 537.7 g of aqueous lactic acid was fed and 512.9 g of product was collected for a 95.4% mass recovery. Likely, CO and water losses in the nitrogen sweep gas account for the shortage in mass balance. This recovery includes 17.3 g material on the lower layer of glass beads which was analyzed and found to be primarily $L_3A$.

The lactide yield was about 78% (when the material on the glass beads is ignored). The L-lactide:meso-lactide weight ratio was found to be about 95:5 for the composite lactide product. The washed LD was about 98% pure and contained less than about 2% $L_2A$. The D-lactide concentration was found to be below the detection limit in LD product isolated from the last recycle.

Thus, the ability to improve yields of lactide by a recycle process while avoiding significant increases in LD racemization has been established.

EXAMPLE 5

In this run, 85% lactic acid (39.3 ml/hr) was passed into the reactor which contained a bed of Amberlyst-15 acid ion-exchange resin held at a nominal bed temperature of 215° C. The nitrogen flow rate was 1580 ml/min, the space time was 2.9 seconds, the feed lactic acid constituted 26.3 wt-% of the total feed, and the superficial velocity through the reactor (screen assembly of Example 3) was approximately 0.11 ft/sec. The results recorded are set forth below:

TABLE 4

| Stage (44934-25) | Cumulative Time (hr) | $L_1A$ Feed (g) | All Products (g) | Crude LD (g) | LD Yield (mole-%) | CO Yield (mole-%) |
|---|---|---|---|---|---|---|
| Equilibration | 1.7 | 74.4 | 36.5 | none | 0 | — |
| 1 | 3.7 | 92.4 | 46.9 | none | 0 | 95 |
| 2 | 5.7 | 84.0 | 28.3 | trace | — | 95 |

This strongly acidic ion/exchange resin gave negligible lactide and almost quantitative decomposition of lactic acid to carbon monoxide (and presumably acetaldehyde). The catalyst bed initially had a very large exotherm (25° C.).

These results are consistent with the results obtained using another Bronsted catalyst (phosphoric acid on Kieselguhr) which showed almost no tendency to generate lactide from lactic acid.

(93:7, respectively) held at a nominal bed temperature of 205° C. The nitrogen flow rate was 1596 ml/min, the space time was 3 seconds, weight percent organic in the feed was 25%, and the superficial velocity was about 0.11 ft/sec. The following results were recorded:

TABLE 6

| Stage (44934-46) | Cumulative Time (hr) | L₁A Feed (g) | All Products (g) | Crude LD (g) | LD Purity (wt-%) | L-LD m-LD | LD Yield (mole-%) | CO Yield (mole-%) | LD Yield CO Yield |
|---|---|---|---|---|---|---|---|---|---|
| Equilibration | 1.5 | 67.2 | 32.2 | 6.37 | — | — | — | — | — |
| 1 | 4.0 | 108.0 | 90.4 | 23.74 | 100 | 23.1 | 32.0 | 2.78 | 11.5 |
| 2 | 6.5 | 105.6 | 92.7 | 18.76 | 100 | 44.9 | 26.0 | 1.74 | 14.9 |
| Post-run | 7.5 | — | 7.3 | | | | | | |
| | | 280.8 | 222.6 | | | | | | |

Catalyst weight gain: 33.93 g (33.0%)
Trap Contents: 2.10 g
Reactor residue: PL₁A in lower T-joint (not weighed)
Total material percent recovery: (>258.6/280.8) (100) > 92.1%
Carbon Monoxide:
2700 ppm after 3.0 hours
1700 ppm after 5.4 hours

EXAMPLE 6

In this run, 85% lactic acid (36.8 ml/hr) was fed to a reactor containing 10-12% molybdenum (VI) oxide on gamma alumina (10-20 mesh) held at a nominal bed temperature of 203° C. A nitrogen flow rate of 1580 ml/min, a space time of 3.0 seconds, the weight percent organics in the feed of 25.2 wt-%, and a superficial velocity of 0.11 ft/sec were maintained in the run. The results recorded are set forth below:

TABLE 5

| Stage (44934-38) | Cumulative Time (hr) | L₁A Feed (g) | All Products (g) | Crude LD (g) | LD Purity (wt-%) | L-LD m-LD | LD Yield (mole-%) | CO Yield (mole-%) | LD Yield CO Yield |
|---|---|---|---|---|---|---|---|---|---|
| Equilibration | 1.5 | 66.0 | 45.5 | 6.4 | — | — | — | — | — |
| 1 | 4.0 | 120.0 | 95.3 | 19.86 | 96.5 | 37.6 | 22.6 | 3.6 | 6.3 |
| 2 | 6.0 | 87.6 | 76.4 | 15.87 | 92.9 | 37.7 | 23.5 | 3.6 | 6.5 |
| Post-run | 7.0 | — | 6.3 | | | | | | |
| | | 273.6 | 222.5 | | | | | | |

Catalyst weight gain: 12.6 g (8.6%)
Trap Contents: 7.63 g
Reactor residue: lactic acid inlet tube filled with PL₁A after cool down
Total material percent recovery: (>242.8/273.6) (100) > 88.8%
Carbon Monoxide:
3,500 ppm after 3.0 hours
3,500 ppm after 5.5 hours The initial exotherm of 9° C. decreased to 1° C. at the end of the run. The observed lactide yields and LD/CO ratios were lower than observed for the silica/alumina catalyst reported above. Accordingly, the next two examples test the effect of the alumina carrier on lactide conversion and its selectivity.

EXAMPLE 7

In this example, 85% lactic acid (36.7 ml/hr) was fed to the reactor having the screen assembly of Example 3 and containing 10-20 mesh gamma alumina/silica gel The initial 15° C. exotherm decrease and the reaction was 2° C. endothermic at the end run. Even though the LD yield dropped during stage 2, a significant drop in CO resulted in the highest LD/CO ratio observed through this run.

EXAMPLE 8

In this run which utilized a reactor having only a lower 16 mesh screen and an upper 42 mesh screen, 85% lactic acid (35.0 ml/hr) was passed through a reactor containing 10-20 mesh of 99% gamma alumina (Alfa, 90 m² g) held at a nominal bed temperature of 204° C. In this run, the nitrogen flow was 1580 ml/min, the space time was 3.03 seconds, the weight percent organic in the feed was 24.3%, and the superficial velocity again was approximately 0.11 ft/sec. The following results were recorded:

TABLE 7A

| Stage (45022-2) | Cumulative Time (hr) | L₁A Feed (g) | All Products (g) | Crude LD (g) | LD Purity (wt-%) | L-LD m-LD | LD Yield (mole-%) | CO Yield (mole-%) | LD Yield CO Yield |
|---|---|---|---|---|---|---|---|---|---|
| Equilibration | 1.5 | 62.4 | 37.52 | 9.54 | — | — | — | — | — |
| 1 | 4.0 | 104.4 | 89.55 | 22.87 | 97.6 | 31.5 | 30.4 | 0.32 | 94.4 |
| 2 | 6.5 | 105.6 | 91.93 | 22.39 | 98.7 | 46.0 | 29.7 | 0.42 | 70.0 |
| Post-run | 7.5 | — | 7.99 | | | | | | |
| | | 272.4 | 227.0 | | | | | | |

Trap Contents: 5.92 g
Catalyst weight gain: 23.88 g (18.3%)
Residue drilled from lower feed lines: 1.66 g
Total material percent recovery: (258.5 g/272.4) 199) = 94.9%

Stages 2 and 3 filtrates were extracted with methylene chloride within one hour after formation to yield the following quantities of lactide:

TABLE 7B

| Sample | Sample wt., (g) | LD Purity (wt-%) | L-LD m-LD | LD Yield (mole-%) | Total LD Yield (mole-%) | Overall LD Composition % L-LD | % m-LD |
|---|---|---|---|---|---|---|---|
| Stage 1 extract. | 2.74 | 91.8 | 5.11 | 3.7 | 34.1 | 95.5 | 4.5 |
| Stage 2 extract. | 3.55 | 92.5 | 4.06 | 4.4 | 34.1 | 95.6 | 4.4 |

Carbon monoxide:
300 ppm after 3.0 hours
400 ppm after 5.7 hours

The initial exotherm of 12° C. reduced to 1° C. after 2.5 hours and was absent after 5 hours. This catalyst serves to distinguish the relative effect of molybdenum (VI) oxide versus alumina in Example 6. Of importance are the relatively high lactide yields that were obtained and especially the high LD/CO ratios that were one order of magnitude higher than previously observed with any other catalyst. These results and those of Example 7 indicate that small silica quantities significantly decrease the LD/CO ratio when using alumina/silica catalysts. Alumina catalyst alone appears to be superior catalyst compared to alumina/silica mixtures.

The filtrates from stages 2 and 3 were extracted with methylene chloride soon after the lactide washing procedures were completed to recover the lactide remaining in solution. These residual lactide samples were found to have lower L-LD/meso-LD ratios compared to stages 1 and 2 lactide due to the preferential solubilization of meso-lactide in cold water. The total lactide yields (obtained from initial washing/filtration followed by filtrate extraction) from both stages is the same (34.1%) and the overall L-LD/meso-LD ratios are the same (95.5:4.5 for stage 1 plus extract and 95.6/4.4 for stage 2 plus extract). If the assumption is made that racemization occurs only in LD and most LD was extracted before it could hydrolyze to $L_2A$, these ratios represent the ultimate L-LD/meso-LD ratio expected after multiple cycles. Interestingly, this ratio appears to approach the 95/5 ratio achieved during the recycle study reported in Example 4.

These results indicate that molybdenum (VI) oxide used in Example 6 may catalyze carbon monoxide formation, or the alumina substrate used for molybdenum (VI) oxide in Example 6 was prepared differently than the gamma alumina used in this example.

EXAMPLE 9

In this example, using the reactor configuration of Example 8, 85% lactic acid (35.3 ml/hr) was passed through the reactor containing 3 mm borosilicate glass beads (washed with water and acetone) held at a nominal bed temperature of 203° C. During this run, the nitrogen flow rate was 1580 ml/min, the space time was 1.15 seconds within the void volume in the glass beads, the weight percent organics in the feed was 20.44%, and the superficial velocity was approximately 0.11 ft/sec. The following results were recorded:

TABLE 8

| Stage (44934-73) | Cumulative Time (hr) | $L_1A$ Feed (g) | All Products (g) | Crude LD (g) | LD Purity (wt-%) | L-LD m-LD | LD Yield (mole-%) | CO Yield (mole-%) | LD Yield / CO Yield |
|---|---|---|---|---|---|---|---|---|---|
| Equilibration | 1.0 | 4.44 | 35.94 | 1.83 | — | — | — | — | — |
| 1 | 3.0 | 87.6 | 71.97 | 82.2 | 5.62 | 96.4 | 8.9 | >.01 | >890.0 |
| 2 | 5.5 | 100.8 | 91.16 | 10.29 | 97.5 | 190 | 14.2 | 0.021 | 670.0 |
| Post-run | 7.2 | 7.2 | 13.03 | — | — | | | | |
| | | 240.0 | 212.1 | | | | | | |

Some glass beads were adhering to reactor walls and were washed free with acetone.
Most beads had a tacky feel. Bead weight gain (after washing): 0.15 g
Trap Contents: 13.94 g
$PL_1A$ which clogged lactic acid feed line and lower fittings after cool down was not weighed.
Total material percent recovery = (>226.04/240) (100) > 94.2%
Carbon Monoxide:
<10 ppm after 2.1 hours
20 ppm after 4.1 hours The approximately 2° C. endotherm was present during the entire run. Some beads had a tacky coating indicating that lactic acid oligomerization was occurring on the glass surfaces.

The use of glass beads without any catalyst resulted in lower LD yields, though much higher L-LD:meso-LD ratios and LD/CO ratios compared to other catalysts tested.

EXAMPLE 10

In this example using the reactor screen configuration of Example 3, 85% lactic acid (35.1 ml/hr) was passed through an empty reactor maintained at a temperature of about 201° C. During this run, the nitrogen flow was 1540 ml/sec; the space time was 10.4 seconds; the weight percent organic in feed was 24.8%; and the superficial velocity was about 0.11 ft/sec. No equilibration period was used in this experiment. The following results were recorded.

TABLE 9

| Stage (44934-70) | Cumulative Time (hr) | $L_1A$ Feed (g) | All Products (g) | Crude LD (g) | LD Purity (wt-%) | L-LD m-LD | LD Yield (mole-%) | CO Yield (mole-%) | LD Yield / CO Yield |
|---|---|---|---|---|---|---|---|---|---|
| One collector used for | 4 | 129.6 | 111.3 | 13.08 | 74.7 | 154 | 11.0 | <0.01 | >1100 |

TABLE 9-continued

| Stage (44934-70) | Cumulative Time (hr) | L₁A Feed (g) | All Products (g) | Crude LD (g) | LD Purity (wt-%) | L-LD m-LD | LD Yield (mole-%) | CO Yield (mole-%) | LD Yield CO Yield |
|---|---|---|---|---|---|---|---|---|---|
| entire run | | | | | | | | | |

Trap contents were not weighed
PL₁A which clogged the lower T-joint and lactic acid feed line after shut-down was not weighed.
Therefore, total material percent recovery > 85.9%
Carbon Monoxide: 10 ppm after 2.5 hours There was no exotherm evident during this run. Lactide yields are approximately the same as reported for the glass bead run of Example 9, but the LD/CO ratio has substantially increased. The low lactide purity of 74.7% resulted due to using a lower than normal proportion of cold wash water due to the relatively small amount of lactide obtained.

Importantly, however, is the conversion of aqueous feed lactic acid into LD using no catalyst or solid packing material in the reactor providing that the LD feed is maintained in the vapor phase at elevated temperature. While LD yields are low, selectivity for LD formation over by-product formation (as measured by the very high LD:CO ratio) and lack of LD racemization (as measured by the high L-LD:meso-LD ratio) appears to be maximized. The effect of alumina catalyst, then, is to improve LD yields, though at the expense of also increasing CO by-product formation and LD racemization. Silica gel and other catalysts likely also improve LD yields, though they increase CO by-product formation to a greater extent. Nevertheless, depending upon the needs of the operator, LD yield maximization or LD selective conversion maximization and control of LD racemization can be obtained by judicious selection of the presence and type of catalyst (and of course temperature).

EXAMPLE 11

This run replicates the empty reactor run in Example 10, except using the reactor screen configuration of Example 8. In this run, 85% lactic acid (34.0 ml/hr) was fed to the empty reactor maintained at about 204° C. The nitrogen flow rate was 1580 ml/sec; the space time was 10.2 seconds; the weight percent organic in feed was 23.7%; and the superficial velocity was approximately 0.11 ft/sec. The following results were recorded.

stage 2 yielded an additional 2.47 g solid which analyzed as 90.5 wt-% LD. This extra increment of LD increases the total LD yield to 15.5% for this stage. This result implies that approximately half of the LD typically generated in runs with catalyst beds could have already formed before contacting the catalyst bed. The precursor of the LD is presumed to be mainly L₂A in the aqueous lactic acid feed which cyclizes and readily vaporizes (or vaporizes/cyclizes) under the reaction conditions. The extra lactide produced when catalysts are employed is presumed to originate from vaporized L₁A which is converted in the chemisorbed state to chemisorbed L₂A which is converted into LD on the catalyst surface. Due to the high vapor pressure of LD compared to that of L₂A, the LD formed on the catalyst surface is rapidly and selectively removed by the heated carrier gas.

The very high L-LD/meso-LD ratios are approximate values since the meso-LD concentration fell below the concentration range used for calibration purposes. However, these L-LD/meso-LD ratios indicate that little or no racemization occurred in this run since the low meso percentages are in the range predicted from the reaction of the approximately 0.3 percent D-L₁A which is present in commercial 85% L-L₁A. The L-LD/meso-LD ratio of extracted stage 2 was found to be approximately 285:1 which indicates that the meso concentration is so low that little selective solubilization of meso-lactide occurs.

These results further indicate that LD can be made without catalyst in high overall yield if L₁A recycle is employed. Furthermore, LD can be made without catalyst with almost complete retention of configuration of the aqueous lactic acid from which it is derived.

We claim:

1. A method for making lactide from aqueous lactic acid feed enriched primarily in L₁A, and L₂A, and some

TABLE 10

| Stage (44934-92) | Cumulative Time (hr) | L₁A Feed (g) | All Products (g) | Crude LD (g) | LD Purity (wt-%) | L-LD m-LD | LD Yield (mole-%) | CO Yield (mole-%) | LD Yield CO Yield |
|---|---|---|---|---|---|---|---|---|---|
| Equilibration | 1.0 | 40.8 | 38.83 | 1.07 | — | — | — | — | — |
| 1 | 3.0 | 84.0 | 70.78 | 5.92 | 97.3 | 280 | 9.7 | <0.001 | >880.0 |
| 2 | 6.0 | 120.0 | 104.05 | 10.89 | 100+ | 206 | 12.9 | <0.001 | >1170.0 |
| Post-run | 7.0 | — | 3.98 | | | | | | |
| | | 244.8 | 217.6 | | | | | | |

Trap Contents: 16.88 g
Entire lactic acid feed line was plugged with PLA after run. Estimated weight: 8.0 g
The lower T-joint had a small amount of oligomeric PA.
Total material percent recovery: (>242.5/244.8) (100) > 99.1%
Stage 2 filtrate (after approximately 18 hours at −5° C.) was extracted with methylene chloride to given 2.47 g white solid which was analyzed and shown to be 90.5 percent lactide with a L-LD/meso-LD ratio of 285. This constitutes an extra 2.6% lactide yield to give a total lactide yield of 15.5 percent from fraction 2.
Carbon Monoxide:
<10 ppm after 2.2 hours
<10 ppm after 4.7 hours Again, no exotherm was observed. These results again show very high LD/CO and L-LD:meso-LD ratios as in Example 10, but also show increasing lactide yield with time. Extraction of the filtrate obtained from L₃A, and depleted in higher L_nA oligomers which comprises the steps of:

(a) converting aqueous lactic acid feed to its vapor phase;
(b) passing said feed vapors through a vapor phase reaction zone maintained at elevated temperature; and
(c) withdrawing from said reaction zone lactide, water, and unreacted aqueous lactic acid feed.

2. The method of claim 1 wherein said elevated temperature ranges from about 150° to 225° C.

3. The method of claim 1 wherein said feed vapors are passed through said vapor phase reaction zone with the aid of a carrier gas.

4. The method of claim 3 wherein said carrier gas comprises nitrogen.

5. The method of claim 1 wherein said vapor phase reaction zone contains an alumina catalyst.

6. The method of claim 1 wherein: step (d) passing said withdrawn lactide, water, and unreacted aqueous lactic acid feed through a cold cyclone for separation.

7. The method of claim 1 wherein any oligomeric lactic acid in said feed is converted to one or more of $L_1A$, $L_2A$, or $L_3A$ with water for its conversion to its vapor phase.

8. The method of claim 1 wherein said lactic acid feed is monomeric lactic acid ($L_1A$).

9. A cyclic process for making lactide from aqueous lactic acid feed enriched primarily in $L_1A$, and $L_2A$, and some $L_3A$, and depleted in higher $L_nA$ oligomers which comprises the steps of:
(a) passing make-up aqueous lactic acid feed into a vaporization zone along with unreacted aqueous lactic acid filtrate from another step of the process and therein forming aqueous lactic acid feed vapors;
(b) passing said vapors through a vapor phase reaction zone held at elevated temperature for forming lactide therein;
(c) separating lactide as a solid from unreacted aqueous lactic acid filtrate; and
(d) passing said filtrate into said vaporization zone in step (a) of the process.

10. The cyclic process of claim 9 wherein said elevated temperature ranges from about 150° to 225° C.

11. The cyclic process of claim 9 wherein said feed vapors are passed through said vapor phase reaction zone with the aid of a carrier gas.

12. The cyclic process of claim 11 wherein said carrier gas comprises nitrogen.

13. The cyclic process of claim 9 wherein said vapor phase reaction zone contains an alumina catalyst.

14. The cyclic process of claim 9 wherein any oligomeric lactic acid in said feed is converted to one or more of $L_1A$, $L_2A$, or $L_3A$ with water for its conversion to its vapor phase.

15. The cyclic process of claim 9 wherein said lactic acid feed is monomeric lactic acid ($L_1A$).

16. The cyclic process of claim 9 wherein said lactide is separated as a solid from unreacted aqueous lactic acid filtrate by filtration by cold centrifuging.

17. The cyclic process of claim 9 wherein said filtrate is subjected to distillation to concentrate the lactic acid content thereof prior to being passed into said vaporization zone.

18. The cyclic process of claim 17 wherein said filtrate is dehydrated by distillation to a degree of polymerization (DP) of not substantially above about 2.

* * * * *

UNITED STATES PATENT AND TRADEMARK OFFICE
CERTIFICATE OF CORRECTION

PATENT NO. :  5,332,839
DATED      :  July 26, 1994
INVENTOR(S) : BENECKE et al.

It is certified that error appears in the above-identified patent and that said Letters Patent is hereby corrected as shown below:

In the Abstract, line 2, delete "invention" and insert therefor --inventive--;

Column 10, line 12, delete "=" and insert therefor -- ± --.

Signed and Sealed this

Twenty-second Day of November, 1994

Attest:

BRUCE LEHMAN

Attesting Officer      Commissioner of Patents and Trademarks